Figure 1:
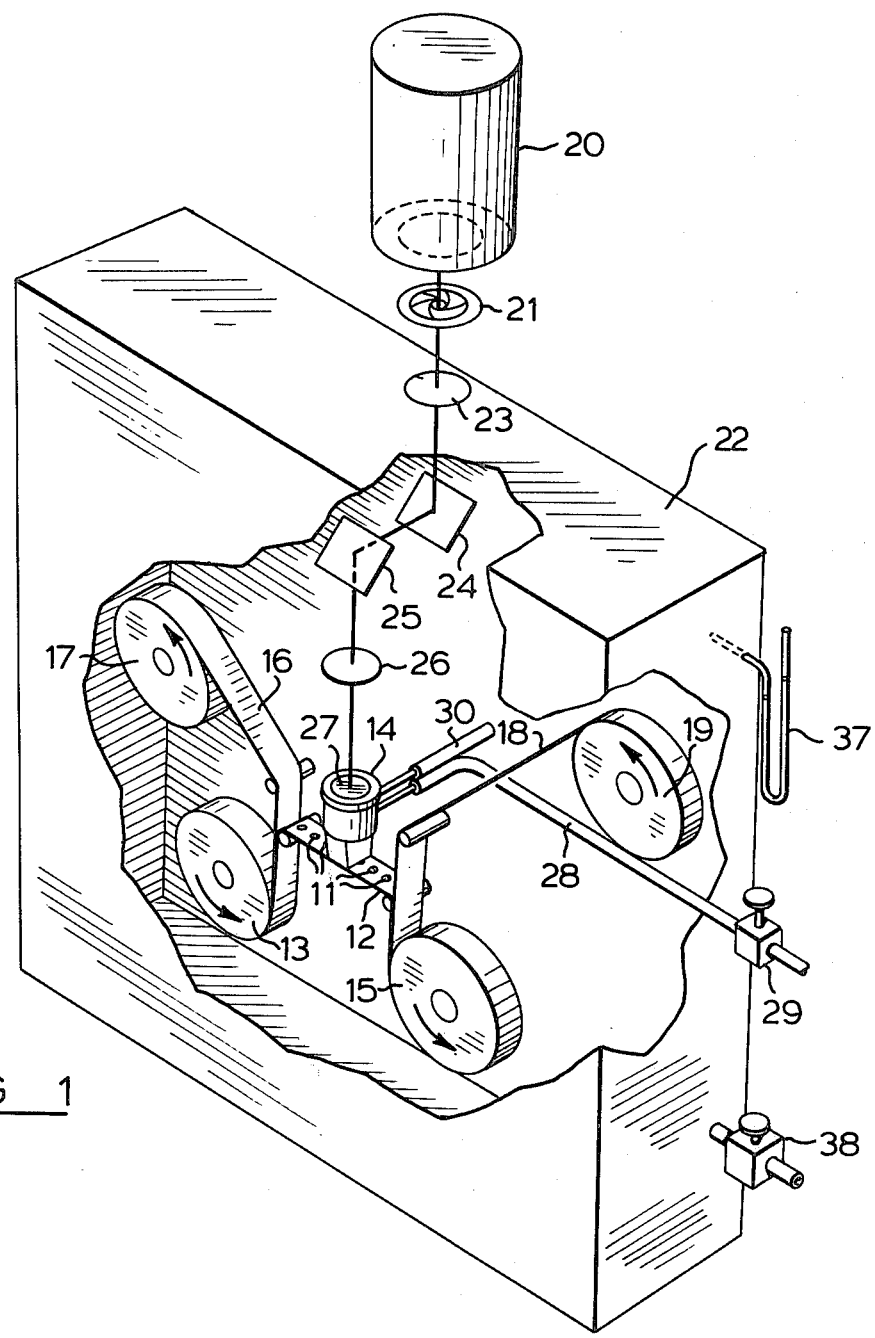

United States Patent [19]

Barringer

[11] 4,220,414

[45] Sep. 2, 1980

[54] LASER SPECTROCHEMICAL ANALYSIS

[75] Inventor: Anthony R. Barringer, Willowdale, Canada

[73] Assignee: Barringer Research Limited, Rexdale, Canada

[21] Appl. No.: 791,766

[22] Filed: Apr. 28, 1977

[30] Foreign Application Priority Data

May 6, 1976 [GB] United Kingdom ............... 18536/76

[51] Int. Cl.³ .......................... G01J 3/30; G01N 1/00
[52] U.S. Cl. ........................................ 356/318; 356/36
[58] Field of Search ....................... 356/36, 73, 85–87

[56] References Cited

U.S. PATENT DOCUMENTS

| | | | |
|---|---|---|---|
| 3,832,060 | 8/1974 | Dahlquist | 356/85 |
| 3,901,599 | 8/1975 | Meric | 356/86 |

FOREIGN PATENT DOCUMENTS 2526679  12/1976  Fed. Rep. of Germany ............ 356/85

*Primary Examiner*—John K. Corbin
*Assistant Examiner*—Wm. H. Punter
*Attorney, Agent, or Firm*—Rogers, Bereskin & Parr

[57] ABSTRACT

A sample of material to be analyzed is applied in a thin layer to a substrate such as an elongated tape and then is illuminated by a laser beam of such wavelength and power that at least a portion of the sample is vaporized. The substrate is non-absorptive at the laser wavelength and therefore is unaffected by the laser beam. The vaporized matter is removed from the region at which vaporization takes place, and is subsequently excited in a plasma to facilitate analysis by a conventional spectrometer.

8 Claims, 3 Drawing Figures

LASER SPECTROCHEMICAL ANALYSIS

This invention relates to the art of chemical analysis, and in particular to a method of analyzing particulates, powdered samples or any other material that can be formed into a thin layer. The invention is applicable to the analysis of samples of soils, minerals, food stuffs or other solid or liquid materials.

Laser beams have previously been used for exciting a sample of matter into vapour form to facilitate spectral analysis, as shown in U.S. Pat. Nos. 3,463,591 to Franken et al and 3,680,959 to Schuch et al. In U.S. Pat No. 3,463,591 a sample to be analysed is energized by a beam of energy from a laser, the resultant vapour being analysed using conventional forms of detection equipment such as a spectroscope or gas chromatograph. In U.S. Pat. No. 3,680,959 a laser plume rising from the sample is caused to enter a gap between a pair of electrodes placed above the sample, reducing the impedence across the electrode gap and causing a spark to bridge the gap. The latter is utilized as an auxiliary means to raise vapour components, not sufficiently excited by a conventional laser, to spectro-emissive energy levels and supplements the radiant emission from the laser plume, the excited matter then being analysed in a spectrograph.

The foregoing techniques have a number of disadvantages. Both techniques are adversely affected by matrix effects which are difficult to predict and control. The Franken et al method suffers from substantial self-reversal and line broadening effects due to the density of the plume, and high radial velocities generated by the explosion of the plume. The latter radial velocities cause extensive Doppler broadening of the emission lines with consequent loss of analytical resolution. When secondary spark excitation is employed, as in Schuch et al, it is necessary to have the spark gap very close to the sample in order to capture a significant proportion of the plume. Under these conditions, additional burning of the sample takes place by heat from the spark and analytical conditions become somewhat uncontrolled. When solid samples are analysed by either of these techniques, the size of the crater formed depends on the absorbtivity and density of the material. The shape of the plume ejected from the surface by the laser varies considerably according to the crater shape. Furthermore, the characteristics of emission from the plume depend upon whether the plume is viewed by the spectrograph on the central axis of the plume or at various distances from the central axis. Each element behaves differently according to the distance from the central axis, so that the optimum positioning of the optical system that is correct for one element, may be incorrect for another.

These problems have been overcome in the present invention. According to one aspect, the invention consists of applying a thin layer of a sample of the material to be analyzed onto a suitable substrate such as a tape (preferably coated with adhesive). The successive samples to be analyzed are placed at spaced-apart locations on the tape, thereby facilitating automated analysis of the samples. Each sample on the tape is vaporized by means of a laser beam of suitable wavelength and power, and the matter thus released from the tape is subsequently analyzed for content of predetermined chemical parameters. Preferably, the wavelength of the laser is chosen so that the laser energy is strongly absorbed by the sample to be analyzed and the adhesive tape or other substrate does not absorb any appreciable amount of energy from the laser and therefore will not be vaporized.

According to another aspect, the invention consists of the method referred to above wherein after each sample has been vaporized, the liberated matter is carried away from the region of the laser plume for subsequent analysis by means of such conventional techniques as emission spectroscopy, mass spectrometry, gas chromatography or the like. Preferably, the liberated matter is carried by means of a stream of an inert carrier gas such as argon into a cell containing a plasma where the matter is thermally excited to temperatures where spectro chemical emission occurs such that spectrographic analysis can be made.

Figure 2:
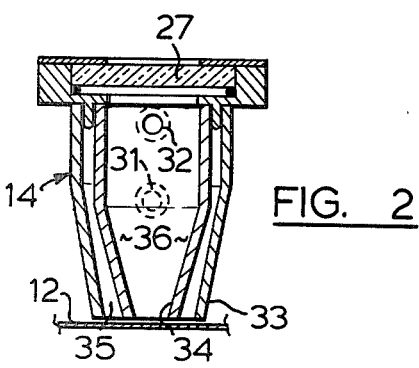
Figure 3:
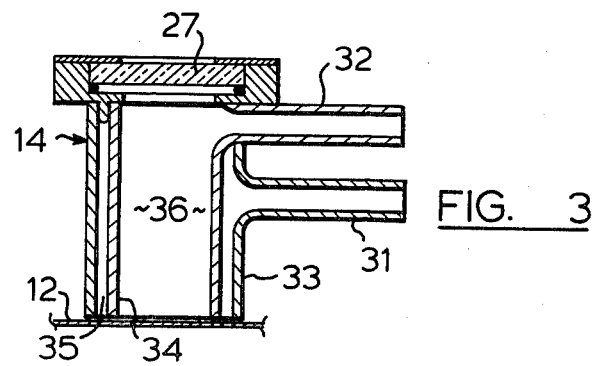

In drawings illustrating a preferred form of apparatus for carrying out the aforesaid methods, FIG. 1 is a diagrammatic perspective view, partly broken away,;

FIG. 2 is a front sectional view of a vaporization cell, as shown in FIG. 1, and FIG. 3 is a side sectional view of the vaporization cell as shown in FIG. 2.

Referring to the drawings, and in particular to FIG. 1, samples of particulate material are deposited as spots 11 on an adhesive tape 12 that can be transported from a storage reel 13 past a vaporization cell 14 to a take up reel 15. As the tape 12 is moved from the storage reel 13 to the take up reel 15 a cover tape 16 is stripped off the tape 12 and is wound up on a take up reel 17. A similar cover tape 18 which may be made of a relatively inert synthetic resin such as polytetrafluoroethylene which is stored on a reel 19, may be applied to the tape 12 as shown in FIG. 1 so that the tapes 12 and 18 are wound up together on the take up reel 15. In this manner, any samples remaining on the tape after analysis may be stored for subsequent reanalysis.

The samples 11 are positioned so that they are subject to irradiation from a laser 20 the beam of which passes through a control iris 21 and enters a housing 22 which encloses the tape mechanism, through a window 23. The laser beam is deflected by means of mirrors 24, 25 down through a focusing lens 26 which serves the function of focusing the laser beam at a point just below the plane of the tape 12. The laser beam passes through a window 27 in the vaporization cell 14. An inert carrier gas such as argon is introduced into the vaporization cell 14 through a pipe 28 via a control valve 29, and the inert carrier gas leaves the vaporization cell via a pipe 30. The vaporization cell is provided with an elongated inlet pipe 31 and outlet pipe 32 which respectively are attached to the pipes 28 and 30. The vaporization cell consists of an outer shell 33 and an inner shell 34 spaced inwardly from the outer shell 33 to define an annular space 35 which communicates with the inlet 31. The shell 34 defines an inner region 36 which is aligned with the window 27 and which is in communication with the outlet 32. The vaporization cell 14 is open at its lower end which is adjacent to the tape 12 so that the regions 35 and 36 of the vaporization cell 14 are open to the tape 12.

When a laser pulse is fired, vaporization of the sample occurs at the point where the laser beam strikes a sample spot 11. The sample spot 11 may be positioned accurately by automatic electro-optical means which may be adapted, for example, to sense the location of registration marks on the tape. The laser beam is sufficiently defocused at the surface of the tape 12 to provide a spot of between about 2 and 4 millimeters in diameter, thus allowing a sample of reasonable size to be vaporized.

The power of the laser, which typically is of the order of 1 joule, is adjusted to be adequate to vaporize a predetermined amount of the sample material without significantly vaporizing the tape.

Some of the inert carrier gas introduced into the vaporization cell 14 from the pipe 28 escapes into the interior of the housing 22 so that the housing 22 becomes filled with the inert carrier gas. The pressure inside the housing 22 is preferably kept slightly above atmospheric pressure as observed on a manometer 37. A valve 38 is provided to permit a controlled leakage of the inert carrier gas from the housing 22 in order to maintain the pressure within the housing 22 at a predetermined level.

Referring now to FIG. 2, it will be observed that the vaporization cell preferably is positioned slightly above the surface of the tape 12, e.g. of the order of 1 millimeter above the surface. Some of the inert carrier gas escapes from the region 35 of the vaporization cell 14 and enters the interior of the housing 22, from which it eventually escapes through the valve 38. The remainder of the inert carrier gas passes into the region 36, from which it passes via outlet 32 into outlet pipe 30. Materials released from the surface of the tape 12 by the laser beam are carried up to the interior of the vaporization cell 14 and out through the pipe 30 into a separate analytical system. By maintaining a steady leakage of inert carrier gas at the surface of the tape 12, any air present in the housing 22 effectively is prevented from becoming entrained in the main flow of gas through the pipe 30 into the analytical system.

The aerosol formed by vaporization of the sample matter by the laser beam and any recondensation of such matter passes out through the pipe 30 into a suitable analyzer, such as an inductively coupled plasma the emission spectra of which is measured by means of a conventional spectrometer.

By way of example, a carbon dioxide laser operating at 10.6 microns may be chosen using a pulsed mode of operation such as that provided by a transverse excited TEA laser. at 10.6 microns most materials, both organic and inorganic, absorb energy strongly, whereas it is possible to chose a substrate such as thin polymer film made of polyethelene, that has a negligible absorption at 10.6 microns. Adhesive tapes are manufactured of this material, such as type 480 manufactured by The Minnesota Mining and Manufacturing Company of St. Paul, Minnesota, U.S.A., which employs a polyethelene base with an adhesive which also exhibits very little absorption at 10.6 microns. Particulate matter that is made to adhere to such tape may be vaporized off the tape with a carbon dioxide laser with little or no vaporization of the tape.

In some cases, it may be desirable to employ a laser the wave length of which is deliberately chosen to vaporize only a selected portion of the sample. Thus, if a ruby laser is employed having a wave length of 6943 angstroms in the visible spectrum, then organic materials containing cellulose, starch and protein will absorb very little energy. On the other hand, any inorganic materials that may be mixed with such organic materials will show strong absorption at such wave length. Thus, analyses of such mixed powders or particulates carried out on the vapors formed by irradiating the sample with a ruby laser at 6943 angstroms will be dominated by the composition of the inorganic constituents with very little effect from the organic constituents. If the same sample is vaporized with a carbon dioxide laser at 10.6 microns, all constituents will absorb energy strongly and the analysis will be indicative of the total composition. From a study of the analysis obtained from both kinds of lasers, it is possible to compute the distribution of various elements between the organic portion that fails to absorb energy at 6943 angstroms and the inorganic portion that absorbs energy at both 6943 angstroms and 10.6 microns.

Such selective vaporization is of importance for example, in the analysis of aerosols. Such aerosols may be impacted onto a transparent adhesive tape and then selectively analyzed for different constituents. Carbonates may be selectively vaporized with a laser pulse of approximately 7 microns. Similarly, elements present as sulphates may be determined by vaporization at wave lengths at which there is strong sulphate absorption.

After each sample is vaporized, two kinds of products are produced. One is an aerosol formed by the rapid condensation of vapors generated from material having high vaporization temperatures and the second kind is vapors which either are driven off from the sample or represent pyrolysis breakdown products, which do not recondense into aerosols after they have been formed. The latter constituents can be introduced directly into vapor analyzing systems such as mass spectrometers and gas chromatographs, while the aerosols normally have to be re-vaporized (for example in a plasma) prior to analysis.

The invention has been described above with reference to the use of transparent adhesive tapes as a substrate. However, an alternative medium is adhesive aluminum tape which has sufficiently high reflectivity to prevent vaporization of the substrate. Furthermore, although it is convenient to use an adhesive tape for holding the samples, it is conceivable that uncoated polyethylene tape may be utilized instead, and in such case electrostatic attraction could be used to fix the samples in position. For particles in the size range of below about 5 microns, adhesive is generally not required as the particles may be impacted directly onto an uncoated plastic substrate or onto aluminum foil. In general, plastics are preferred over aluminum or other metallic foil as a tape medium since they tend to be free of trace metals to a greater extent so that minor vaporization of the substrate does not affect the analysis to any significant extent. It is comparatively more difficult, for example, to obtain aluminum foil with adequate purity. In general, whether the substrate is a tape or else a smaller carrier such as a glass slide, the requirement is that the material of the substrate should either totally reflect the laser beam or else should be made of a material which does not appreciably absorb the laser energy.

In general, the smaller the particle, the easier it is to vaporize the particle in its entirety. Conversely, heavier particles may not be completely vaporized by a single laser pulse, and matrix effects (which lead to measurement errors) usually occur in such circumstances.

A technique which has been employed with some success in respect of heavier particles (of the order of 200 microns and greater) is to apply the laser beam successively to the sample sample and integrate the results of successive analyses.

What I claim is:

1. A method of analyzing samples of material for predetermined chemical parameters comprising:

(a) depositing a sample of said material in a thin layer on a substrate, said substrate having an adhesive coating to which such material adheres, (b) irradiating said sample with a laser beam focused on said sample at a region where vapourization of said sample occurs, the wavelength and intensity of said laser beam and the thickness of said sample being such that at least a portion of said sample is vapourized by said laser beam, said laser wavelength being selected so that a substantial portion of the energy of the laser beam is absorbed by said sample and substantially none of said laser energy is absorbed by said substrate or by said adhesive, so that said substrate and said adhesive are substantially non-absorbent of energy at the wavelength of said laser beam, whereby said portion of said sample may be vapourized without vapourizing said substrate or said adhesive, and (c) analyzing the vapourized sample for said predetermined chemical parameters.

2. A method as claimed in claim 1 wherein after said sample has been irradiated, the vapourized material is removed from said region and said vaporized sample is analyzed at a location separated from said region.

3. A method as claimed in claim 2 wherein after said sample has been vapourized, said sample is injected into a stream of an inert carrier gas and is transported to a plasma where it is excited to facilitate spectrographic analysis.

4. A method as claimed in claim 1, wherein substantially all of said sample is vapourized with a single pulse of said laser beam.

5. A method as claimed in claim 1, wherein substantially all of said sample is vapourized with successive pulses of said laser beam.

6. A method as claimed in claim 3 wherein said samples are deposited at spaced-apart locations on said substrate, and said substrate comprises a tape which is movable step-wise to expose successive samples to said laser beam.

7. A method as claimed in claims 1 wherein said material is in the form of particulates, wherein said particulates are deposited on said substrate substantially one particle thick, and wherein said particulates are below about 100 microns in diameter.

8. A method as claimed in claims 6 wherein said material is in the form of particulates, wherein said particulates are deposited on said substrate substantially one particle thick and wherein said particulates are below about 50–60 microns in diameter.

* * * * *